(12) United States Patent
Schlangen et al.

(10) Patent No.: US 10,932,345 B2
(45) Date of Patent: Feb. 23, 2021

(54) LIGHTING SYSTEM

(71) Applicant: SIGNIFY HOLDING B.V., Eindhoven (NL)

(72) Inventors: Lucas Josef Maria Schlangen, Eindhoven (NL); Vanja Hommes, Assen (NL); Marina Cecilia Gimenez, Groningen (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 15/326,921

(22) PCT Filed: Jul. 10, 2015

(86) PCT No.: PCT/EP2015/065898
§ 371 (c)(1),
(2) Date: Jan. 17, 2017

(87) PCT Pub. No.: WO2016/008826
PCT Pub. Date: Jan. 21, 2016

(65) Prior Publication Data
US 2017/0208673 A1 Jul. 20, 2017

(30) Foreign Application Priority Data
Jul. 17, 2014 (EP) ..................................... 14177533

(51) Int. Cl.
*H05B 47/16* (2020.01)
*H05B 45/10* (2020.01)
(Continued)

(52) U.S. Cl.
CPC ............. *H05B 47/16* (2020.01); *A61M 21/00* (2013.01); *A61N 5/0618* (2013.01); *H05B 45/10* (2020.01);
(Continued)

(58) Field of Classification Search
CPC ............ H05B 37/0281; H05B 37/0218; A61N 2005/0626; A61N 2005/0651;
(Continued)

(56) References Cited

U.S. PATENT DOCUMENTS

2003/0095476 A1  5/2003  Mollicone et al.
2007/0268234 A1  11/2007  Wakabayashi et al.
(Continued)

FOREIGN PATENT DOCUMENTS

EP   1886708 A1    2/2008
JP   2013254702 A  12/2013
(Continued)

OTHER PUBLICATIONS

A. Borisuit, "The Impact of Light Including Non-Image Forming Effects on Visual Comfort", Ph.D, École Polytechnique Fédérale De Lausanne, 2013. (Year: 2013).*
(Continued)

*Primary Examiner* — Lynsey C Eiseman
*Assistant Examiner* — Amanda L Steinberg
(74) *Attorney, Agent, or Firm* — Meenakshy Chakravorty

(57) ABSTRACT

There is provided a lighting system for illuminating a space, the lighting system comprising: at least one light source; and at least one controller configured to: receive an indication of a pre-selected duration of an emission period for which the at least one light source is to emit light; control the at least one light source to emit light for the duration of the emission period, select a first spectrum in dependence on the duration of the emission period, and control the at least one light source to emit the light with the first spectrum during at least part of the emission period. There is also provided a display apparatus, a method and a computer program product.

16 Claims, 4 Drawing Sheets

(51) Int. Cl.
*H05B 45/20* (2020.01)
*H05B 47/11* (2020.01)
*H05B 47/105* (2020.01)
*A61M 21/00* (2006.01)
*A61N 5/06* (2006.01)
*A61M 21/02* (2006.01)

(52) U.S. Cl.
CPC .......... *H05B 45/20* (2020.01); *H05B 47/105* (2020.01); *H05B 47/11* (2020.01); *A61M 21/02* (2013.01); *A61M 2021/0044* (2013.01); *A61N 2005/0626* (2013.01); *A61N 2005/0651* (2013.01); *A61N 2005/0663* (2013.01); *Y02B 20/40* (2013.01)

(58) Field of Classification Search
CPC .. A61N 2005/0663; A61M 2021/0044; A61M 21/00
See application file for complete search history.

(56) References Cited

U.S. PATENT DOCUMENTS

| | | | |
|---|---|---|---|
| 2008/0170476 A1* | 7/2008 | Hurst | A61M 21/00 368/250 |
| 2009/0207028 A1* | 8/2009 | Kubey et al. | A61M 21/00 368/250 |
| 2010/0063566 A1 | 3/2010 | Uchiumi et al. | |
| 2010/0277316 A1* | 11/2010 | Schlangen | A61M 21/00 340/540 |
| 2012/0069551 A1 | 3/2012 | Bues et al. | |
| 2012/0101554 A1 | 4/2012 | Feather et al. | |
| 2013/0119891 A1 | 5/2013 | Herremans et al. | |

FOREIGN PATENT DOCUMENTS

| | | |
|---|---|---|
| WO | 2005004948 A2 | 1/2005 |
| WO | 2007116341 A1 | 10/2007 |
| WO | 2008110959 A1 | 9/2008 |
| WO | 2008146219 A1 | 12/2008 |
| WO | 2008146220 A2 | 12/2008 |
| WO | 2009090596 A1 | 7/2009 |
| WO | 2012011008 A1 | 1/2012 |

OTHER PUBLICATIONS

S. Chellappa, R. Steiner, P. Blattner, P. Oelhafen, T. Götz and C. Cajochen, "Non-Visual Effects of Light on Melatonin, Alertness and Cognitive Performance: Can Blue-Enriched Light Keep Us Alert?", PLoS ONE, vol. 6, No. 1, p. e16429, 2011. Available: 10.1371/journal.pone.0016429. (Year: 2011).*

* cited by examiner

LIGHTING SYSTEM

CROSS-REFERENCE TO PRIOR APPLICATIONS

This application is the U.S. National Phase application under 35 U.S.C. § 371 of International Application No. PCT/EP2015/065898, filed on Jul. 10, 2015, which claims the benefit of European Patent Application No. 14177533.8, filed on Jul. 17, 2014. These applications are hereby incorporated by reference herein.

FIELD OF THE INVENTION

The invention relates to a lighting system, a display apparatus comprising the lighting system, a method of controlling a light source and a computer program product.

BACKGROUND

In addition to its use in sight, light powerfully regulates the so-called biological, non-visual (or non-image forming, NIF) responses of humans and other mammals. In particular, the human eye comprises a receptor located in the retina that is based on the photopigment melanopsin (the "melanopsin receptor"). The melanopsin photopigment has, for humans, a peak wavelength sensitivity for the blue portion of the visible spectrum. The human eye contains a sensory system that comprises several other photopigments (rods and cones) next to melanopsin. The light impinging on these receptors regulates the circadian system of humans and other mammals, as well as the acute effects of light (e.g. an increased alertness and melatonin suppression). Melatonin is a hormone that varies in a daily cycle, allowing the chronobiological entrainment of the circadian rhythm of several biological functions.

European patent application publication number EP 1,886,708 A1 discloses a method of controlling a lamp to support circadian rhythm. The light is emitted with a spectral composition and intensity that is a function of the time of day between sunrise and sunset.

SUMMARY

It is an object of the following to provide a lighting system, an apparatus comprising the lighting system and a method of controlling a light source.

According to a first embodiment there is provided a lighting system for illuminating a space, the lighting system comprising: at least one light source; and at least one controller configured to: receive an indication of a pre-selected duration of an emission period for which the at least one light source is to emit light, control the at least one light source to emit light for the duration of the emission period, select a first spectrum in dependence on the duration of the emission period, and control the at least one light source to emit the light with the first spectrum during at least part of the emission period.

The at least one controller may be configured to control the lighting system to select the first spectrum in further dependence on an intensity of the light to be emitted during the emission period and/or the time of day during which the emission period lies.

The at least one controller may be configured to control the lighting system to select the first spectrum in further dependence on: an intensity and/or spectrum from one or more other sources illuminating an area adjacent to the space illuminated by the lighting system, and/or a duration of the light emitted from the one or more other sources and/or the state of the circadian clock of a user within said space during the emission period.

The at least one controller may be configured to select a first spectrum in dependence on the duration of the emission period by selecting spectral components of light to be emitted and intensities thereof.

The intensity of the light emitted during the emission period may be pre-selected prior to the determination of the first spectrum, the first spectrum being selected in response to the pre-selected intensity.

At least one of the duration of the emission period and/or the intensity of the light to be emitted during the emission period may be pre-selected by a user.

The emission period may be pre-selected from a range between 5 seconds and 2 hours.

The intensity of the first spectrum may be less than 18m-lux and, in dependence on this intensity, the at least one controller may be configured to include a spectral component having a wavelength of 505 nm.

The at least one controller may be configured to generate the first spectrum in dependence on whether the light is to be emitted continuously or discontinuously during the emission period. The light may be emitted discontinuously in pulses of 10 minutes and the spectral composition of light is matched to an m-cone absorption spectrum.

The at least one controller may be configured to generate the light so as to suppress spectral components responsible for melatonin suppression in humans.

The at least one controller may be operable to set a start and/or end point of the emission period.

There is also provided a display apparatus comprising a lighting system as described in any of the above.

There is also provided a method of controlling at least one light source, the method comprising: receiving an indication of a pre-selected duration of an emission period for which the at least one light source is to emit light, controlling the at least one light source to emit light for the duration of the emission period, selecting a first spectrum in dependence on the duration of the emission period, and controlling the at least one light source to emit the light with the first spectrum during at least part of the emission period.

There is further provided computer program product embodied on at least one computer-readable storage medium and configured so as when executed on one or more processors of a lighting system to perform operations of: receiving an indication of a pre-selected duration of an emission period for which the at least one light source is to emit light, controlling at least one light source to emit light for at least the duration of the emission period, selecting a first spectrum in dependence on the duration of the emission period, and controlling the at least one light source to emit the light with the first spectrum during at least part of the emission period.

These and other aspects are apparent from and will be elucidated with reference to the embodiments described hereinafter.

BRIEF DESCRIPTION OF THE DRAWINGS

In the drawings.

Items having the same reference numbers in different figures have the same functional features. If the function of such an item has been explained, there is no necessity for repeated explanation thereof in the detailed description as the skilled person is already considered to be enabled.

DETAILED DESCRIPTION

Non-visual responses to light are mediated by retinal transduction pathways that have a non-constant reaction to impinging light. Instead, the response of the retinal transduction pathways varies with the intensity and duration of the light exposure. Therefore the action spectrum for these responses is not fixed. By exploiting this effect, a lighting system located in an area can be configured to engender a targeted biological reaction in a user located in that area.

In particular, the following discloses a system in which the composition of a light spectrum (which can comprise at least one of the selection of spectral components and the intensity of each spectral component) produced by a lighting system can be adapted in dependence on the exposure duration used or set. In embodiments, the system allows a user (e.g. an end-user or a designer of the system) to pre-select a predetermined time program for controlling the lighting for some other reason than its photo-biological effect. For example, the user may set a certain wake-up light scheduled to come on around the time the user plans to wake up (e.g. the light may be programmed to come on once with a continuous emission or in pulses of a few minutes to gradually wake up the user). Depending on the duration of the exposure that the user has set, the system will then automatically adapt the spectrum of this light to additionally provide a more optimal photo-biological effect such as suppressing the secretion of the hormone melatonin.

In another example, the user triggers the lights to turn on or dim up, either explicitly by activating an explicit user control, or by triggering a presence sensor which in turn triggers the lights when the user is detected to be present. If the user leaves the lights on or dimmed up for longer than a certain threshold duration of time, or remains present so that the presence sensor continues to keep the lights on or dimmed up for longer that a certain threshold duration of time, the system may adapt the spectrum of the light to produce a more optimal photo-biological effect given the length of time the lights have been on or dimmed up.

Further, in embodiments the system may also allow a user to select the intensity of the light emitted by the lighting system, and a combination of the exposure duration and the selected intensity of light to be emitted may influence the selection of a composition of a light spectrum to be emitted by a lighting system.

Current lighting systems do not adapt the composition and/or the intensity of a light spectrum produced by a lighting system in dependence on the exposure duration used or set (N.B. in EP 1,886,708 the spectrum is a function of time of day but does not depend on the exposure duration).

Figure 1:
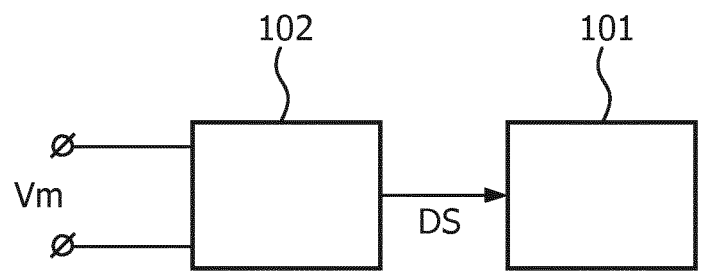
FIG. 1 schematically shows a block diagram of a lighting system.

FIG. 1 schematically shows a block diagram of a lighting system. The lighting system comprises at least one light source 101 and at least one controller 102 that drives the light source 101 to emit light with a varying spectrum. For example the light source 101 may comprise a plurality of lighting elements such as LEDs which emit different colours, allowing the spectrum to be controlled by turning the different coloured elements (e.g. LEDs) on and off in different combinations, and/or controlling their relative intensities.

The controller 102 comprises a driver which receives an input voltage and supplies a current and/or voltage DS to the light source 101. The driver receives the AC mains voltage Vm and has an electronic circuit for controlling the current through or the voltage across the light source 101. The controller 102 is thus able to control when the light source 101 turns on and off, and/or the intensity with which it emits light when on. The controller 102 is also able to control the spectrum with which the light source 101 emits light when on. For example if the light source 101 comprises different coloured LEDs, the spectrum of the combined light can be varied by changing the ratio of currents through or voltages across the LEDs. Usually, LEDs are current driven. In other examples, circuits that vary the spectrum of a single lamp by, for example, changing the frequency of duty-cycle of the current through or the duration across the single lamp, can be used to control the spectrum of combined light from multiple lamps.

The controller 102 also comprises control functionality for controlling the timing with which the light source 101 is turned on and off and/or varies its intensity, and also for selecting the spectrum with which the light source 101 emits (via the driver circuitry discussed above). The control functionality may be implemented in software stored in one or more storage media of the system, and arranged for execution on one or more processors of the system; or alternatively the control functionality may be implemented in dedicated hardware circuitry, or configurable or reconfigurable circuitry such as a pin grid array or Field Programmable Gate Array; or any combination of such software and circuitry.

The control functionality of the controller 102 comprises a timer (implemented in hardware or software) arranged to control the light source 101 to emit for a first, defined period of time, an emission period, and also to control the spectrum (intensity and/or components thereof) with which the light source 101 emits its light during the emission period in dependence on a pre-selected duration of the emission period.

Where it is said the (at least one) light source 101 is controlled to emit during an emission period, this may mean either turning the light source 101 on or dimming it up, having been turned off or dimmed down immediately prior to the emission period and also being turned off or dimmed down immediately following the emission period. The light source may be controlled to emit continuously during the emission period, or the light source may be controlled to emit light in a train of light pulses during the emission period. The light source 101 may be controlled to emit with a single, constant spectrum of light during the emission period, or may be controlled to emit such that the spectrum of light varies during the emission period. In the case of a train of pulses, the light source may be controlled to emit no light between each light pulse in the train, or emit at a dimmed-down level. The light pulses may have the same spectrum as each other or a different spectrum to each other. Examples of these various embodiments are described below.

The controller may control the light source 101 to emit light having the selected spectrum during the entire emission period. Alternatively, the controller may control the light source 101 to emit light having a selected spectrum for just a part of the emission period (e.g. a later part). For example, where the controller receives an advance notification that light will be emitted for at least 10 minutes, the controller 102 determines in advance that the spectrum is to be varied after, for example, 7 minutes to engender a particular NIF response using certain receptors.

In the case where the spectrum varies within the emission period, the controller may determine to periodically or aperiodically vary the spectrum in that emission period so as to cause a pulsing colour light to be emitted from the light source 101 (alternatively or in addition to pulses in intensity, e.g. on-off pulses). During that emission period, there may or may not be instances in which no light is being emitted. For example, where the spectrum is to be varied, the light source 101 may be controlled to emit no light before emitting the changed spectrum.

It is noted that the control functionality of the controller may be configured to provide a static and/or a time-varying control of a light source in dependence on the duration for which the light source emits light over an emission period. Either way, the static spectrum or time-varying profile of the spectrum is determined in advance based on knowledge of a pre-selected (e.g. user-selected) duration for which the light source is going to emit light. This control may involve selecting at least a first spectrum (including spectral components and (optionally) individually selecting intensities of the spectral components) in dependence on the duration of the emission period.

In embodiments the timer (implemented in hardware or software) may also be operable to set the starting instant and/or end instant of the emission period mentioned above. The controller may comprise an input for receiving a command setting the duration of the emission period, or indicating that an emission period of a selected duration should begin. The command may be a user command, which may be input to the controller via a user interface.

In one example, the controller 102 is configured to control the at least one light source 101 to emit light according to a predetermined time program defining at least the duration of the emission period, and optionally the start and/or end points of the emission period, and/or times or durations of other periods when the light source is on or off or dimmed up or down. For example, said schedule may further define an off period immediately prior to and/or after the emission period, during which the at least one controller turns off the at least one light source. The controller 102 may be arranged to receive an indication of the time schedule including at least the duration of the emission period (and any other timing of the light source) from a user via a user interface to which the controller 102 is connected. For instance the time schedule may set the timing of a wake-up light, or a daily light profile in an environment such as a school, hospital or elderly care institution. In such cases, the user has set the time schedule of the lighting for some other reason such as to provide a wake-up light in the morning or prior to work, or to save energy by only turning on the lights at certain times. The controller 102 additionally adapts the spectrum of the light to provide a more appropriate biological response given the timing that the user has selected (e.g. enhancing or reducing stimulation of melanopsin, or other photopigments, as a result of the light exposure).

In another example the controller 102 is configured to trigger the start of the emission period ("on" period) in response to an event, and to dynamically adapt the spectrum in response to how long the lights stay on. For example, the controller 102 may receive a user input via an explicit user control indicating that the light source 101 is to be turned on or dimmed up, and in response the first timer period also starts running. If the controller 102 does not receive a complementary user input to turn off or dim down the light source 101 before a certain time has elapsed, such that the emission period has exceeded a certain threshold, then the controller 102 adapts the spectrum of the light to produce a more appropriate biological effect given the length of time the lights have been on so far (e.g to enhance or reduce stimulation of melanopsin, or other photopigments, as a result of the light exposure). In a similar example, the controller 102 is connected to a presence sensor which can detect the presence of a user. The controller 102 automatically turns on or dims up the light source 101 when it detects the user presence or user action, and automatically turns off or dims down the light source 101 if no user presence is detected. In this case, the controller 102 can also begin timing the emission period when presence is detected (and so when the lights are turned on or dimmed up). If the user is detected to remain present for longer than a certain time, such that the lights have remained on and the emission period has exceeded a certain threshold, the controller 102 again adapts the spectrum of the light output accordingly.

In further embodiments, the controller 102 may be further configured to control the lighting system to generate the first spectrum of light during the emission period in dependence on at least one of: a preselected intensity of the first spectrum of light, a light source emission in the immediate vicinity of the lighting system, a light exposure duration in the immediate vicinity of the lighting system during a time period immediately prior to the emission period and/or the time of day in the immediate locality of the light source controlled by the lighting system. Immediate vicinity here means the light from another source encroaches on the space illuminated by the lighting system and/or falls in a region immediately outside of the space illuminated by the lighting system. For an example of the latter case, one may consider how a light in a previous room (such as a corridor) affects the user's response to new light in a new room when selecting a spectrum for the new light. In yet further embodiments, the controller 102 may be further configured to control the light source 101 to generate a spectrum selected for the emission period in further dependence on whether the emitted light is pulsed or continuous during the emission period.

The following presents information on the retinal-transduction pathways.

Under normal conditions, light is the main stimulus that influences the circadian system. Melanopsin receptors (i.e. melanopsin containing retinal ganglion cells (RGCs—nerve cells whose body is outside the central nervous system)) play an important role in mediating this influence via so-called biological, nonvisual responses to light. The melanopsin action spectrum in humans shows a peak sensitivity at about 460-480 nm.

The retinal-transduction pathway response to impinging light depends on the time of day, circadian phase, light history and the intensity and duration of the light exposure. Various photoreceptors, including rods, cones and melanopsin receptors, contribute to signal formation to the suprachiasmatic nucleus (SCN) (the SCN plays a role in the brain in the circadian rhythm) that results from a complex interplay between these different retinal photoreceptors.

Figure 2:
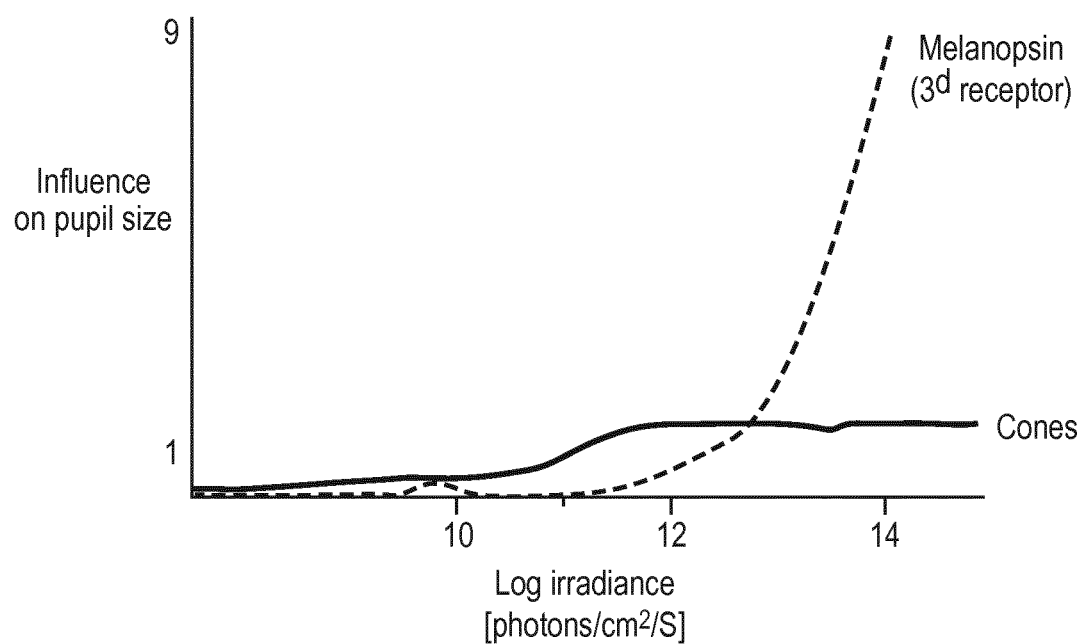
FIG. 2 shows an influence of melanopsin receptors and cones on pupil size as a function of the logarithm of irradiance.

The pupil response is under the control of both the cones and the melanopsin (third receptor). This is illustrated in FIG. 2, which demonstrates the relative influence of cones and melanopsin receptors on pupil size (y-axis) as a function of logarithmic irradiance (in photons/cm$^2$/s) along the x-axis. As the pulse durations increase (i.e. as the cumulative irradiance doses increases), the melanopsin receptors have a much greater influence on the pupil size than the cone receptors. At lower levels of irradiance, the cone receptors have a greater influence on the pupil size than the melanopsin receptors. In mice that have been genetically modified to comprise red cones (modified using knock in, a genetic engineering method that involves the insertion of a protein coding cDNA sequence at a particular locus in an organism's chromosome), the cones account for all pupil responses at low irradiances (<$10^{12}$ photons/cm$^2$/s: for 4000K light, this photon density corresponds to about 2 lux). At higher irradiances, cones play a reduced role. It is at this point that melanopsin phototransduction in the retinal-transduction pathways via melanopsin receptors becomes the dominant driver for pupil response. For longer exposure durations, the red cone contribution to the pupil response drops and the melanopsin sensitivity increases.

The synchronisation of the circadian rhythm is mediated by direct input from the intrinsically photosensitive retinal ganglion cells (ipRGCs) in the eye. Rods, cones and melanopsin receptors can all contribute to the input coming out of the ipRGCs. The functional contributions of rods, cones and retinal circuits to these ipRGCs are not fully understood. Experiments in mice that lack functional rods, or in which rods are the only functional photoreceptors, showed that rods were solely responsible for photoentrainment (i.e. alignment of a circadian rhythm of an organism to light) at low light levels. This means that at low light intensities the action spectrum for photoentrainment is dominated by the rod action spectrum. This peaks at roughly 505 nm in humans.

Rods are also capable of driving circadian photoentrainment at photopic intensities (i.e. intensities used in normal daylight) at which they are incapable of supporting visually guided behaviour. Using mice in which cone photoreceptors were ablated, it was found that rods signal through cones at high light intensities but not at low light intensities. Thus rods use two distinct retinal circuits to drive ipRGC function to support circadian photoentrainment across a wide range of light intensities.

Research has also shown that in the first quarter of a 6.5 hour lasting nocturnal light exposure, 555 nm light was equally effective as 460 nm light at suppressing melatonin secretion. This suggests a significant contribution from the three-cone visual system ($\lambda_{max}$=555 nm) during this part of the light exposure. However, during the latter part of the light exposure, the spectral sensitivity to 555 nm light decayed exponentially relative to the 460 nm light.

Moreover, for phase-resetting responses at lower photon densities (<$10^{12.5}$ photons/cm$^2$/s), green light appeared to be more effective compared to blue light. This is reversed at higher photon densities. In other words, at higher intensities (>$10^{12.5}$ photons/cm$^2$/s), blue light tends to be more effective than green light for phase-resetting responses. This is depicted in FIG. 3.

Figure 3:
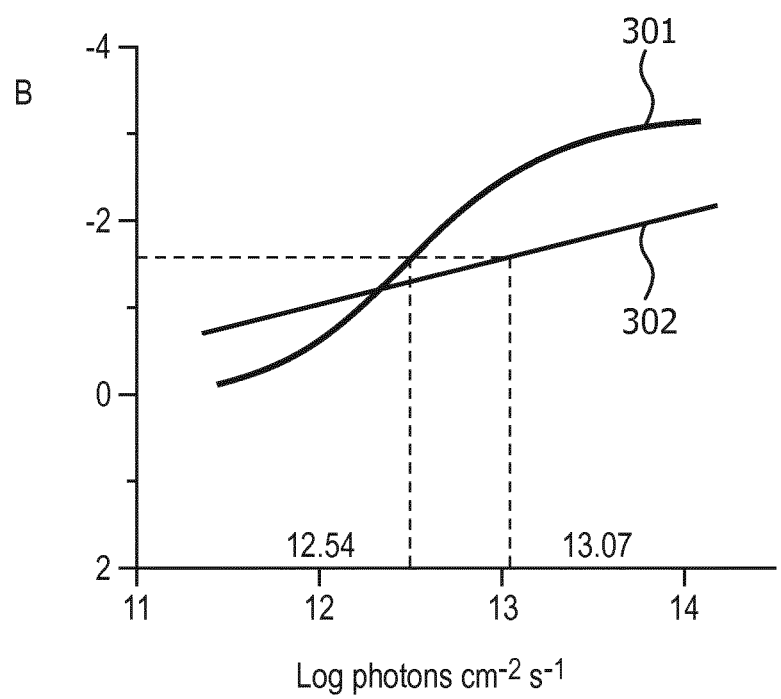
FIG. 3 shows circadian phase shifts in response to retinal exposure of different wavelength light as a function of the logarithm of irradiance.

FIG. 3 depicts circadian phase shifts in response to retinal exposure to 460 nm (blue light, indicated as 301) and 555 nm (green light, indicated as 302) of various photon densities. The horizontal dashed line depicts the half-maximal phase-shift response. The vertical dashed lines depict the corresponding log half-maximum-response-values (ED50), which are indicated on FIG. 3 adjacent to their respective dashed line. Although the log ED50 for phase shifting to 555 nm light tends to be higher than the response to 460 nm light, the difference in log ED50 values is not statistically significant.

Rods can react to light in approximately 20 ms. However, it can take melanopsin receptors about 50 ms to react to changes in light. Further, cones can decrease the reaction of time of melanopsin receptors to the presence of light whilst rods can improve it. This is because the melanopsin receptors are very slow at switching off after light exposure, and cones do not saturate for high light exposures. Cones react fastest when detecting the absence of light and then act on the melanopsin system to signal that the lights are off. In contrast, rods are sensitive at very low light levels and provide a signal to the melanopsin system that the light is on.

At high light intensities (>500 lux) all photoreceptors will be activated and the melanopsin photoreceptor action spectrum (which peaks at around 440-480 nm) is expected to largely dominate the spectral sensitivity of non-image forming response(s). However, at intermediate and low light intensities, different photoreceptors may be operative at different moments of the light exposure.

Melanopsin receptors are quite sluggish in their responses, both towards lights on and lights off. At medium/high intensities of incident light, melanopsin is always important.

Rods can enhance melanopsin ipRGC firing (as mentioned above). Rods are sensitive at very low light levels and signal to the melanopsin ipRGCs that a light is on before melanopsin receptors are able to signal itself that the light is on.

Cones do not saturate for high light exposures and can inhibit melanopsin ipRCG firing. Cones are fastest in detecting the absence of light and act on melanopsin ipRCGs to signal lights off. The melanopsin system is very slow in switching off after light exposure. Thus without the cone input, the melanopsin system is very slow in switching off after light exposure. There are three kinds of cones, S, M and L cones, each with its own absorption peak of 445, 545 and 570 nm respectively (small, medium and large wavelength respectively). The joint three cone visual system drives photopic vision as characterized by the V lambda spectral curve (which is a measure of spectral luminous efficiency) that peaks at 555 nm. The circadian system is able to integrate photons over tens of minutes allowing discontinuous stimuli to be used to evoke circadian phase shifts. Cones show rapid and extensive adaptation under extended illumination, but they attain a steady-state polarization, the magnitude of which is intensity dependent. Consequently, while there is an a priori expectation that light adaptation would impact cone input to the clock, this need not preclude cones from supporting photo-entrainment and other NIF functions. The influence of cones on non-image forming functions (like circadian entrainment) depends upon the temporal pattern of the light exposure. In mice with red cone opsin. m-cones (Opn1mwR—In Opn1mwR mice, the native mouse m-cone opsin is lost and replaced with a human red cone opsin whose spectral sensitivity profile is quite distinct from that of mouse rod, melanopsin and s-cone opsins), discontinuous light stimuli (such as, for example, 650 nm at CT16 presented as 15×1 min pulses over 43 min) are substantially more efficient in achieving phase delays as compared to one 15 minute pulse of equal photon density (~100×). This shows that cones provide input to the circadian system during discontinuous light pulses.

When a pulse of light is initially incident on a user's eye (e.g. between a lights-off and a lights-on situation), the rods, cones and melanopsin receptors react in different ways depending on the intensity and/or duration of the light exposure. The rods have a relatively constant response to the newly incident light, contributing a flat-line signal in the formation of the signal output to the SCN. The cone response has an initial spike shortly after the lights are switched on. This spike decreases linearly with time and/or intensity. In contrast, the melanopsin receptors start to provide a response shortly after the spike in the cone response. The melanopsin receptor response starts from zero and increases linearly with time. At some point in time, the signal contribution to the SCN from the melanopsin receptors overtakes the signal contribution to the SCN from the cones.

In mice, non-image forming (NIF) effects of light exposures above 1.8 m-Lux are almost exclusively determined by melanopsin receptors. In humans this threshold is expected to correspond to 18 m-lux. Underneath this threshold rods dominate NIF responses (see Table 1). In this context, the unit m-lux refers to melanopic-lux. For m-lux, the emission spectrum from a light source is weighted for its ability to stimulate the melanopsin photoreceptor. M-Lux is defined in the paper "A "melanopic" spectral efficiency function predicts the sensitivity of melanopsin photoreceptors to polychromatic lights" by Enezi et al (J Biol Rythms 2011 Ag; 26(4) 312-23).

The situation at higher irradiances, within the melanopsin sensitivity range (i.e., above 18 m-lux), is more complex. Cones remain sensitive and support vision under even the brightest illumination. In species in which cone vision is spectrally quite distinct from that of melanopsin (e.g., humans), cones may therefore strongly influence the spectral sensitivity of ipRGC-driven NIF responses. Under most daylight conditions, melanopsin is expected to be the primary influence on ipRGC activity.

The photoreceptor pathways for different NIF functions may also depend on different subtypes of retinal ganglion cells.

TABLE 1

Contributions of the different photoreceptors to ipRCG mediated non-image forming responses for different light exposures

| Light exposure | Rod receptors (505 nm) | Cone receptors (555 nm) | Melanopsin (480 nm) | ipRCG signal |
| --- | --- | --- | --- | --- |
| Low intensity (<18 m-Lux) | dominate | Not active | Not active | Rod driven (505 nm) |
| Medium intensity (>18 m-lux and <50 lux) | Not (saturated) | active | active | Cone and melanopsin driven (480 + 555 nm) |
| High intensity (>50 lux) | Not (saturated) | active | Most active | Melanopsin driven (480 nm), probably w/o role cone |
| Discontinuous intensity (repeated light pulses of <10 min) | Not active | m-cone active | active | M-cone & melanopsin driven |

Thus, in the presently described system, when the system is used at a certain exposure duration of light level, it is configured to automatically select a spectral composition (which may include automatically selecting respective intensities for the selected spectral components) that matches the action spectrum of the photoreceptors that is most active for this light condition in determining the non-image forming response. This system can take into account the information provided in table 1 regarding the relative contributions of rods, cones and melatonin containing retinal ganglion cells as a function of light intensity (and/or duration).

In one example, when coming from the dim light adapted state, the lights-on signal (i.e. when the light intensity is suddenly increased) to the ipRGCs is mainly given by rods. The "lights-on" rod signal continues to be of relevance for the duration of the light pulse. The "lights-off" signal (i.e. when the light is removed or is otherwise suddenly reduced) is given by cones. At higher light intensities, where cones are activated, cones play a role in signalling irradiance for NIF functions. However, this is rapidly taken over by melanopsin receptors, making melanopsin receptors the main photoreceptor input to the SCN signaled by the retinal ganglion cells (RGCs). Rods may play the predominant role in driving responses at night and around dawn/dusk, with melanopsin taking over throughout most daylight. Light adaptation would limit cone influence under most conditions. However, this may allow cones to encode a somewhat different aspect of the light environment. Thus, the relatively sluggish adaptation recorded herein for melanopsin receptors would, in effect, introduce a high-pass filter, reducing the influence of the tonic component of cone activity under continuous illumination in favour of more phasic responses to sudden changes in irradiance. This would free cones to provide higher-frequency modulation of pupil size. The circadian clock, because of its long integration time for photic information, would be relatively refractory to these transient cone signals except under conditions of high temporal contrast i.e. pulsing, or otherwise discontinuous light. When referred to pulsing, it is understood that the light pulses may be periodic or aperiodic. It is also understood that the duration of each light pulse may vary. This would be advantageous if the targeted biological reaction of the user located in the area served by the lighting system changes over time.

In further experiments, various irradiances and durations were tested for their ability to suppress nocturnal melatonin and promote alertness. Table 2 specifies the light conditions used.

TABLE 2

Light conditions used in the monochromatic irradiance-duration studies Wavelengths studied $\lambda_{max}$ 437, 479, 555 nm

| Light duration (min) | Photon flux (photons/cm$^2$/s) IM | Total photon content (photons/cm$^2$) TP |
| --- | --- | --- |
| 10 | $3.0 \times 10^{13}$ | $1.8 \times 10^{16}$ |
| 20 | $3.0 \times 10^{13}$ | $3.6 \times 10^{16}$ |
| 30 | $3.0 \times 10^{13}$ | $5.4 \times 10^{16}$ |
| 10 | $9.0 \times 10^{13}$ | $5.4 \times 10^{16}$ |
| 20 | $4.5 \times 10^{13}$ | $5.4 \times 10^{16}$ |

Figure 4:
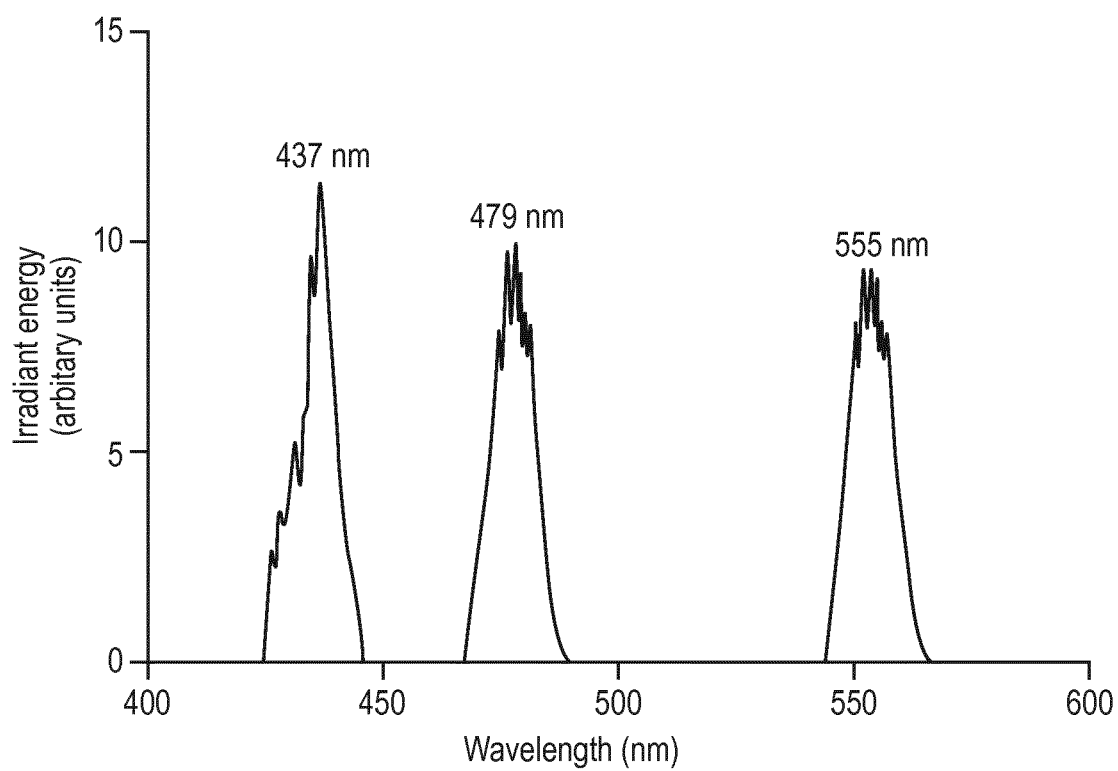
FIG. 4 shows irradiant energy at three different wavelengths.

To generate this table, three monochromatic lights were used with $\lambda_{max}$ at 437, 479 and 555 nm. This is represented in FIG. 4, where the wavelength of each of the three peaks is labelled next to their respective peak. In total five light conditions were investigated for each wavelength. Three light pulses were matched for irradiance ($3.0 \times 10^{13}$ photons/cm$^2$/s), but varied in duration (10, 20 or 30 min) resulting in a different total photon content. An additional two light conditions were tested that were 10 and 20 min in duration and administered the same total photon content as the 30 min light pulse ($5.4 \times 10^{16}$ photons/cm$^2$/s) as a (2).

Figure 5A:
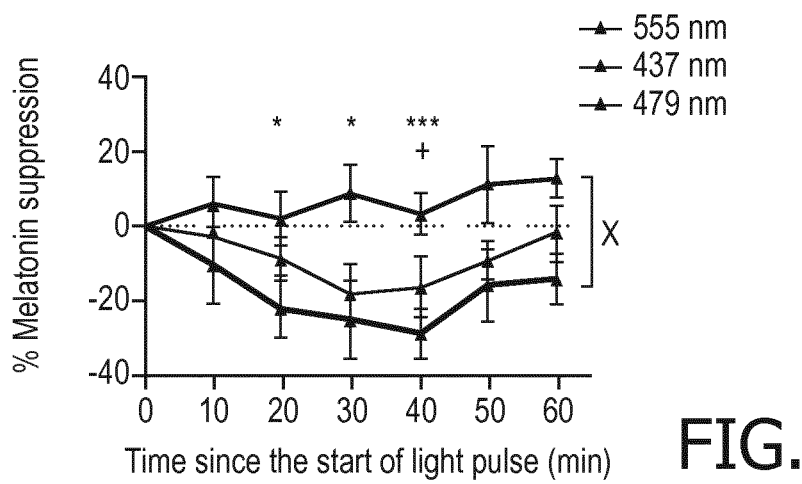
FIGS. 5A to 5C show melatonin suppression for different wavelengths as a function of a time in minutes since a pulse.
Figure 5B:
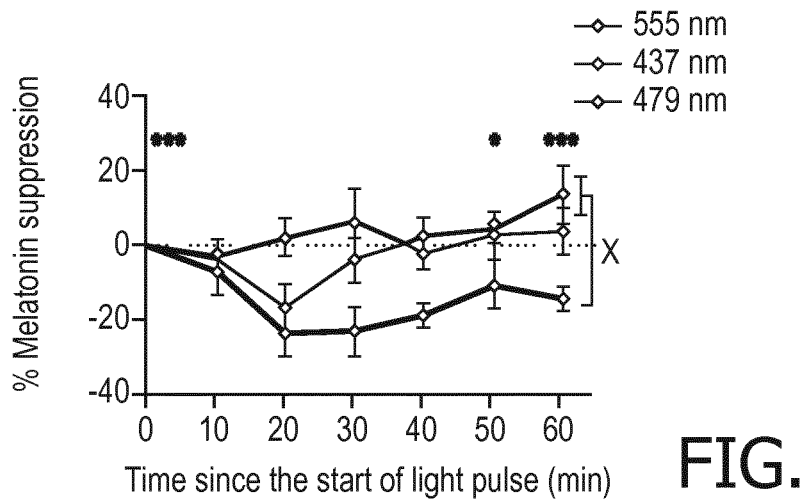
Figure 5C:
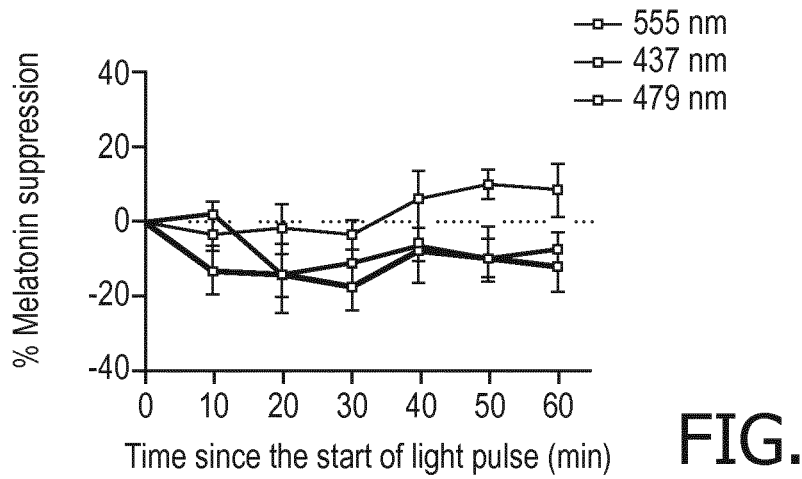

To further illustrate these effects, we refer to FIGS. 5A to 5C. These figures depict a percentage melatonin suppression (mean±SEM) over time during irradiance or total photon content matched λmax 437, 479 and 555 nm light pulses of different durations.

FIG. 5A corresponds to a thirty minute pulse duration with an intensity irradiance of $3 \times 10^{13}$ photons/cm$^2$/s. The x-axis represents the time since the start of the light pulse in minutes. The y-axis represents a percentage of Melatonin suppression. In this example, 479 nm is a more effective wavelength than 437 nm for suppressing melatonin.

FIG. 5B corresponds to a ten minute pulse duration with an intensity irradiance of $3 \times 10^{13}$ photons/cm$^2$/s. The x-axis represents the time since the start of the light pulse in minutes. The y-axis represents a percentage of Melatonin suppression. In this example, 437 nm is a more effective wavelength than 479 nm at supressing nocturnal melatonin.

FIG. 5C corresponds to a twenty minute pulse duration with an intensity irradiance of $3 \times 10^{13}$ photons/cm$^2$/s. The x-axis represents the time since the start of the light pulse in minutes. The y-axis represents a percentage of Melatonin suppression. In this example, 437 nm and 479 nm wavelengths are about equally effective at suppressing nocturnal melatonin.

In relation to these findings, it is noted that cone photoreceptors appear to contribute more to non-visual (or non-image forming) responses at the beginning of a light exposure and at low irradiances. However, during long-duration light exposure and at high irradiances, melanopsin appears to be the primary photopigment driving circadian responses.

Thus, knowing the variance of the phototransduction pathways and how they vary with exposure-intensity, the spectral composition of a light exposure can be set for enhancing a particular biological effect. This spectral composition can be set using wavelength, duration and intensity.

As discussed, according to the present disclosure, there is provided a controller 102 for controlling the lighting of an area, and in particular the spectral composition of the lighting. The controller 102 is configured to control the spectral composition and/or the intensity of the light produced by the lighting system in dependence on the duration of the light exposure, e.g. the intended duration of use as indicated by a user of the lighting system.

In embodiments, the spectrum and/or intensity of the light output may depend on the temporal contrast of the lighting, for example depending on whether the light output comprises discontinuous light stimuli or light pulses. For example, the light pulses may be less that 10 minutes and may be repeated. This can be selected by a user or may be otherwise configured to match an absorption spectrum of, for example, the m-cone (i.e. the cone that responds best to medium-wavelength light). At low intensities (i.e. below 18 m-lux), the predetermined time program may comprise a first time interval of between 5 seconds and 5 minutes. The predetermined program may comprise a first time interval of between 5 seconds and 30 minutes. The predetermined program may comprise a first time interval of between 5 seconds and 2 hours. In this first time interval, the spectrum may be enriched with cone activating light (approximately 505 nm).

In further embodiments, the spectrum and/or intensity of the light output may also depend on the light intensity of the area to be lit by the lighting system.

The following presents different examples.

Example 1

In this example, the controller 102 is configured to select a spectral composition with the aim of maximising melatonin suppression in a user located within the lighting area controlled via the predetermined time program for different light exposure durations. Consequently, a predetermined time period of the pulse length is taken as the predetermined emission period for configuring the spectral composition.

When the pulse duration is short (i.e. less than 10 min) and low intensity the devices automatically uses 437 nm light.

When the pulse duration is long (more than 30 min), the device automatically uses 479 nm light. This arrangement exploits an effect displayed in FIGS. 5A to 5C.

Example 2

In this example, the controller 102 is configured to change the spectral composition over time with the aim of maximising melatonin suppression in a user within the lighting area controlled via the predetermined time program.

If the user sets the emission period to longer than 10 minutes, then during the first interval of the emission period (e.g. for the first 10 minutes) the device automatically uses 437 nm light. After 10 minutes, the device may automatically switch to 479 nm light. This technique exploits the effect displayed in FIGS. 5A to 5C.

If on the other hand the user sets to emission period to shorter than 10 minutes, the device automatically uses 437 nm light for the entire duration.

It is noted that alertness can develop differently from melatonin suppression. It has been found that for exposures longer than 10 minutes, light having components around 437 nm are more effective at inducing alertness than other wavelengths.

Example 3

In this example, a predetermined time program is pre-configured based on knowledge of the emission duration taken into account as a method step performed by the system designer at the design stage. The predetermined program is configured to change the spectral composition over time with the aim of maximising melatonin suppression in a user within the lighting area controlled via the predetermined time program. This system aims to use rods to support the ipRGCs response to newly incident light (i.e. during a "lights-on" scenario). In this embodiment, it is assumed that the user has set the time of the emission period to cover at least three intervals: the first interval, the intermediate period and the second interval detailed below.

During the first interval of the emission period (ranging from 0 to approximately 1-5 min), the predetermined program is configured to cause 437 nm and 505 nm spectral components to be used by the lighting system. The latter (505 nm) component is selected to use rods for extra ipRCG support. After the first time interval, there is an intermediate period in which the predetermined program uses light having a spectral component of around 437 nm. An intermediate period starts after expiry of the first interval and lasts for up to 5 minutes. At the end of the intermediate period, there is a second time interval during which the lighting system is configured to have light having a spectral component of 479 nm. This type of arrangement exploits the effects outlined in relation to Table 1.

Example 4

In this example, the predetermined time program is configured to change the spectral composition over time with the aim of restricting the nocturnal melatonin suppression in a user within a lighting system. It may do this by recruiting cones to support the ipRGC response to the absence of light.

During the last interval of a an emission period of a light pulse of duration $t_1$, where $t_1$ is set by e.g. a user, the predetermined time program may be configured to include extra 555 nm spectral components in the light emitted by the lighting system. This spectral component utilises cones to signal the end of the light exposure by means an extra "lights off" cone input pathway to the ipRGCs. When any melanopsin activation has occurred, this has the effect of reducing the melanopsin activation in a shorter time period after ending the pulse. This allows for, assuming the lighting system is being used at night time when users of the system desire sleep, a reduction in the melatonin suppression action of the ipRGCs, which enables a faster return to sleep for the user following a nocturnal awakening or bathroom visit. This technique is advantageously applied for light pulses that are designed to minimise or otherwise reduce melatonin suppression, for instance a light pulse that avoids using any blue light around 480 nm, or one that uses only light having a wavelength greater than 530 nm light. The last interval may have its own associated duration of between 1 and 5 minutes from the end of the emission period.

Example 5

In this example, the predetermined time program is configured to change the spectral composition over time, in dependence on the duration for which the light source is configured to emit light, to restrict or enhance the nocturnal melatonin suppression by a lighting system that emits white light.

Example 5 is similar to the examples mentioned above. However, there is an additional cone or rod input receptive to light pulses of white light of various colour temperatures. For example, the spectral composition and intensity can be changed over time to enhance circadian phase shifting by a lighting system e.g. a light system that includes a discontinuous cone (m-cone, with 545 nm absorption peak) addressing light component with an emission period of less than 10 minutes. The cone component may be inactive for at least 50% of the time. The cone component may be inactive for at least 30% of the time.

Figure 6:
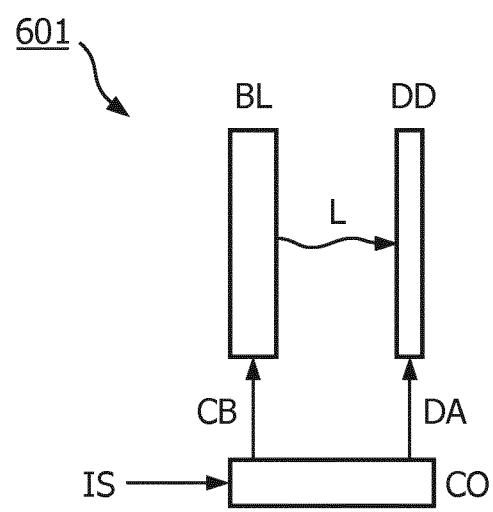
FIG. 6 schematically shows a display apparatus.

In embodiments the lighting system takes the form of a system for illuminating a space such as a room or outdoor space. However, the system may also be implemented in other forms. FIG. 6 schematically shows an alternative implementation in a display apparatus. The display apparatus 601 comprises the backlight unit BL, a pixilated display device DD, and a controller CO. The controller CO receives the input signal IS, which represents an image, and supplies data and control signals DA to the display device DD, and a control signal CB to the backlight unit BL. The image may be a natural scene (photo, video) or may be computer generated. The control signal CB controls the spectrum of the light source(s) 1 in the backlight unit BL. The controller CO may comprise a timer to control the timing of the different phases of the sequence of the different spectra S1 and S2. The backlight unit BL may comprise the controller 102 (see FIG. 1), which provides the current/voltage to the light source(s) 101 to obtain the light L for illuminating the display device DD. For example, the display device DD is an LCD or DMD. For example, the back light unit may comprise fluorescent tube(s) and/or LEDs.

The present lighting system and apparatus described herein may be implemented in several applications, such as for example: office lighting (e.g. to improve early morning activity and to reduce after-lunch fatigue), hospital lighting (e.g. to reduce sleep inertia of medical staff upon nocturnal wake-up), care home lighting (e.g. to reduce day-time napping of elderly to improve nocturnal sleep duration and sleep quality), control rooms (e.g. to obtain sustained alertness during 24 hours operation and night shift work) and automotive lighting (e.g. alternating in-car exposure to low intensity red and blue LEDs to improve driver alertness). The particular biological response in a user located within the area to be lit by the lighting system is used to select the spectrum (in addition to the duration). The particular biological response may be input by an intended user of the system (e.g. the user intended to experience the particular biological response). The particular biological response may be input by a system administrator who is not the intended recipient of the particular biological response.

It should be noted that the above-mentioned embodiments illustrate rather than limit the invention, and that those skilled in the art will be able to design many alternative embodiments without departing from the scope of the appended claims.

For example, the light sources may comprise a full spectrum light emitting device and (switchable) filters to generate the different spectra. Such filters may comprise electrochrome, electrophoretic, liquid crystal cells comprising (dichroic) dyes or based on electrowetting.

The present system may be combined with existing dynamic lighting systems. For example, a sequence of sub-sequences is added in the morning to further improve the alertness of the subject. The first sub-sequence of this sequence has the three phases, while the successive sub-sequences have three or two phases. Such existing dynamic lighting systems vary the color temperature and intensity of a light source over the day. However, these prior art lighting systems do not provide the sequences of the three phases, and change the color temperature of the emitted light very slowly during transition periods of one hour or more.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A lighting system for illuminating a space, the lighting system comprising:
  a light source comprising a plurality of lighting elements which are configured to emit different colors; and
  at least one controller configured to:
  receive an indication of a pre-selected total duration of an emission period for which the first light source is to emit light, the total duration of the emission period comprising a first time period and a second time period;
  control the light source to emit light during the first and second time periods, wherein the at least one controller is configured to control the light source to emit light with a composition of a first light spectrum comprising a first wavelength during the first time period of the total duration, wherein the first wavelength is selected at least in part on the total duration of the emission period, the first time period, and an action spectrum of photoreceptors that dominate in providing a non-image forming response, wherein the composition of the first light spectrum is suitable for generating a non-visual response at a user;

adapt the light emitted by the light source during the second time period such that the light source emits light with a composition of a second light spectrum comprising a second wavelength selected at least in part based on the total duration of the emission period, the second time period, and an action spectrum of photoreceptors that dominate in providing a non-image forming response; and wherein the at least one controller is configured to control the lighting system to adapt the compositions of the first light spectrum and the second light spectrum in further dependence on the state of the circadian clock of a user within said space during the emission period, and an intensity or spectrum of illumination measured by a light sensor of an area adjacent to the space illuminated by the lighting system.

2. The lighting system as claimed in claim 1, wherein the at least one controller is configured to adapt the composition of the first light spectrum in dependence on the first time period and total duration of the emission period and the second light spectrum in dependence on the second time period and total duration of the emission period by selecting spectral components of light to be emitted and intensities thereof.

3. The lighting system as claimed in claim 1, wherein the intensity of the light emitted during the total emission period is pre-selected prior to the adaptation of the composition of the first light spectrum, the composition of the first light spectrum being adapted in response to the pre-selected intensity.

4. The lighting system as claimed in claim 1, wherein at least one of the total duration of the emission period and the intensity of the light to be emitted during the total emission period is pre-selected by the user.

5. The lighting system as claimed in claim 1, wherein the first time period or the second time period of the total emission duration is pre-selected from a range between 5 seconds and 30 minutes.

6. The lighting system as claimed in claim 5, wherein the intensity of the first light spectrum or the second light spectrum is less than 18m-lux and wherein, in dependence on this intensity, the at least one controller is configured to include a spectral component having a wavelength of 505 nm.

7. The lighting system as claimed in claim 1, wherein the at least one controller is configured to adapt the composition of the first light spectrum or the second light spectrum in dependence on whether the light is to be emitted continuously or discontinuously during the emission period.

8. The lighting system as claimed in claim 7, wherein the light is emitted discontinuously in pulses of 10 minutes and the spectral composition of the light is matched to an m-cone absorption spectrum.

9. The lighting system as claimed in claim 1, wherein the at least one controller is configured to adapt the composition of the first light spectrum or the second light spectrum wherein spectral components responsible for melatonin suppression in humans are suppressed.

10. The lighting system as claimed in claim 1, wherein the at least one controller is operable to set a start point or end point of the emission period.

11. A display apparatus comprising a lighting system as claimed in claim 1.

12. A method of controlling a light source, the method comprising:

receiving an indication of a pre-selected total duration of an emission period for which the light source is to emit light, the total duration of the emission period comprising a first time period and a second time period;

controlling the light source comprising a plurality of lighting elements which are configured to emit different colors, to emit light with a composition of a first light spectrum comprising a first wavelength during the first time period, wherein the method comprises selecting the first wavelength at least in part based on the total duration of the emission period, the first time period, and an action spectrum of photoreceptors that dominate in providing a non-image forming response, wherein the composition of the first light spectrum is suitable for generating a non-visual response at a user;

adapting the light emitted by the light source during the second time period such that the light source emits light with a composition of a second light spectrum comprising a second wavelength, wherein the method comprises selecting the second wavelength at least in part based on the total duration of the emission period, the second time period, and an action spectrum of photoreceptors that dominate in providing a non-image forming response; and and further adapting the compositions of the first light spectrum and the second light spectrum in further dependence on the state of the circadian clock of a user within said space during the emission period, and an intensity or spectrum of illumination measured by a light sensor of an area adjacent to the space illuminated by the lighting system.

13. A computer program product embodied on at least one non-transitory computer-readable storage medium and configured so as when executed on one or more processors of a lighting system to perform operations of the method of claim 12.

14. The method of claim 12, further comprising adapting the composition of the first light spectrum in further dependence on a duration of the illumination measured by the light sensor.

15. The lighting system as claimed in claim 1, wherein the non-image forming response is input by an intended user of the lighting system.

16. The method of claim 12, wherein the non-image forming response is input by an intended user of the lighting system.

* * * * *